United States Patent
Fremont

(10) Patent No.: US 10,151,695 B2
(45) Date of Patent: Dec. 11, 2018

(54) OPTICAL ASSURANCE CAP

(71) Applicant: Jiffy-tite Co., Inc., Lancaster, NY (US)

(72) Inventor: Bradley C. Fremont, Tonawanda, NY (US)

(73) Assignee: Oetiker NY, Inc., Lancaster, NY (US)

( * ) Notice: Subject to any disclaimer, the term of this patent is extended or adjusted under 35 U.S.C. 154(b) by 1 day.

(21) Appl. No.: 15/461,002

(22) Filed: Mar. 16, 2017

(65) Prior Publication Data

US 2018/0266950 A1 Sep. 20, 2018

(51) Int. Cl.
| | |
|---|---|
| *G01N 21/00* | (2006.01) |
| *G01N 21/59* | (2006.01) |
| *G02B 5/00* | (2006.01) |

(52) U.S. Cl.
CPC ........... *G01N 21/59* (2013.01); *G02B 5/003* (2013.01); *F16L 2201/30* (2013.01); *G01N 2201/08* (2013.01)

(58) Field of Classification Search
CPC ....... F16L 37/088; F16L 37/138; F16L 21/08; F16L 37/08; F16L 37/38; F16L 37/084; F02M 35/10091
USPC .......................................... 356/432–440, 246
See application file for complete search history.

(56) References Cited

U.S. PATENT DOCUMENTS

| | | | |
|---|---|---|---|
| 6,271,753 B1 | 8/2001 | Shukla | |
| 6,494,617 B1 | 12/2002 | Stokes et al. | |
| 7,061,382 B2 | 6/2006 | Claessens et al. | |
| 7,298,274 B2 | 11/2007 | Chen et al. | |
| 7,400,247 B2 | 7/2008 | Hopman et al. | |
| 7,541,932 B2 | 6/2009 | Lee et al. | |
| 7,696,886 B2 | 4/2010 | Lai | |
| 7,839,288 B2 | 11/2010 | Wang et al. | |
| 8,120,484 B2 | 2/2012 | Chrisholm | |
| 8,485,359 B2 | 7/2013 | Anderson | |
| 8,735,856 B2 | 5/2014 | Lolla et al. | |
| 8,964,186 B2 | 2/2015 | Cheim | |
| 9,107,820 B2 | 8/2015 | Mintchev et al. | |
| 9,228,919 B1 | 1/2016 | Hawwa et al. | |
| 2007/0252008 A1 | 11/2007 | Rowe | |
| 2008/0238675 A1 | 10/2008 | Yang | |
| 2011/0042557 A1 | 2/2011 | Mossman | |
| 2012/0000858 A1 | 1/2012 | Butler et al. | |
| 2015/0032253 A1 | 1/2015 | O'Dougherty et al. | |

(Continued)

FOREIGN PATENT DOCUMENTS

| | | |
|---|---|---|
| CN | 103185198 A | 7/2013 |
| CN | 103424593 A | 12/2013 |

(Continued)

*Primary Examiner* — Hoa Pham
(74) *Attorney, Agent, or Firm* — Simpson & Simpson, PLLC

(57) ABSTRACT

An optical assurance cap, having a body including a through-bore, a first section having a first light absorption coefficient, a second section having a second light absorption coefficient, and a third section having a third light absorption coefficient, operatively arranged between the first section and the second section, wherein the first and second light absorption coefficients form a first combined light absorption coefficient, and the first, second, and third light absorption coefficients form a second combined light absorption coefficient, the first combined light absorption coefficient being less than the second combined light absorption coefficient.

36 Claims, 11 Drawing Sheets

(56) References Cited

U.S. PATENT DOCUMENTS

| | | | |
|---|---|---|---|
| 2015/0145240 A1* | 5/2015 | Kujawski | F16L 37/02 |
| | | | 285/33 |
| 2015/0345684 A1* | 12/2015 | Kujawski, Jr. | F02M 35/10091 |
| | | | 285/86 |
| 2016/0061802 A1 | 3/2016 | Criel et al. | |
| 2016/0238173 A1* | 8/2016 | Kujawski, Jr. | F16L 37/413 |
| 2017/0114935 A1* | 4/2017 | Kujawski, Jr. | F16L 37/088 |
| 2017/0254453 A1* | 9/2017 | Fremont | F16L 55/11 |

FOREIGN PATENT DOCUMENTS

| | | | |
|---|---|---|---|
| GB | 2521857 A | 7/2015 | |
| KR | 1020090097821 A | 9/2009 | |
| KR | 100927464 B1 | 11/2009 | |

\* cited by examiner

OPTICAL ASSURANCE CAP

FIELD

This disclosure relates generally to an assurance cap for a fluid connector, and, more specifically, to an assurance cap for a fluid connector including sections having different light absorption coefficient coefficients arranged within the cap to allow position testing of the cap with optical light to reduce possible leak paths of the fluid connector. This disclosure also relates to a light emitter and sensor in order to test the cap on the fluid connector.

BACKGROUND

Fluid connectors are integral components for many applications, and especially for automotive applications. Since an automotive system is made up of various components such as a radiator, transmission, and engine, fluid must be able to travel not only within each component but also between components. An example of fluid traveling between components is the transmission fluid traveling from the transmission to the transmission oil cooler in order to lower the temperature of the transmission fluid. Fluid predominantly moves between components via flexible or rigid hoses which connect to each component by fluid connectors.

When fluid connectors are secured to devices such as radiators, tubular connectors inserted into these fluid connectors may not be fully seated and allow leak paths to form once the assembly is pressurized. Current tubular connectors include a witness bead which is used as a visual indicator of proper sealing, but these witness beads are not always reliable as it is dependent on a human user to check.

In addition to a witness bead, an assurance cap may be used to further secure and verify the tubular connector is properly inserted into the fluid connector. The assurance cap is installed concentrically about the tubular connector and snaps over an outer circumference of the fluid connector. In some instances, the assurance cap may only partially secure to the fluid connector since these fluid connectors are typically installed in the confined spaces of an engine bay of an automobile. Moreover, a user may not be able to hear the audible "click" sound when the assurance cap fully secures to the fluid connector, leading to the tubular connector blowing out of the fluid connector since it was not fully installed.

Thus, there has been a long-felt need for an assurance cap which can be secured to a fluid connector which allows a user to physically inspect and ensure that the assurance cap is properly seated such that the tubular connector is secured within the fluid connector.

BRIEF SUMMARY

The present disclosure broadly comprises an optical assurance cap, having a body including a through-bore, a first section having a first light absorption coefficient, a second section having a second light absorption coefficient, and a third section having a third light absorption coefficient, operatively arranged between the first section and the second section, wherein the first and second light absorption coefficients form a first combined light absorption coefficient, and the first, second, and third light absorption coefficients form a second combined light absorption coefficient, the first combined light absorption coefficient being less than the second combined light absorption coefficient.

Additionally, the present disclosure broadly includes an optical assurance cap having a body including a through-bore, a first inner circumferentially arranged channel, and a second inner circumferentially arranged channel, a first section having a first light absorption coefficient, arranged within the first inner circumferentially arranged channel, and a second section having a second light absorption coefficient, arranged within the second inner circumferentially arranged channel.

Even further, the present disclosure broadly includes a fluid connector assembly, including a fluid connector having a through-bore, an optical assurance cap arranged on the fluid connector, the optical assurance cap including a first section having a first light absorption coefficient, a second section having a second light absorption coefficient, comprising a shoulder to engage the fluid connector, a third section having a third light absorption coefficient, arranged between the first section and the second section, wherein the first and second light absorption coefficients form a first combined light absorption coefficient, and the first, second, and third light absorption coefficients form a second combined light absorption coefficient, the first combined light absorption coefficient being less than the second combined light absorption coefficient, and a through-bore operatively arranged in the first section, the second section, and the third section, aligning with the through-bore of the fluid connector, and a tubular connector arranged in the through-bore of the fluid connector and secured to the fluid connector by a wire clip, which is further retained by the optical assurance cap.

Even further, the present disclosure broadly includes a fluid connector assembly, including a fluid connector having a through-bore, an optical assurance cap arranged on the fluid connector, the optical assurance cap comprising a through-bore, a tubular connector arranged in the through-bore of said fluid connector and secured to the fluid connector, and a tester tool including a channel, a light source, and a light sensor, the light source and the light sensor axially displaced from one another, wherein the optical assurance cap is arranged in the channel of the tester tool.

Even further, the present disclosure broadly includes a method of determining if an optical assurance cap is fully seated on a fluid connector, the method including installing a tubular connector into a through-bore of the fluid connector, installing the optical assurance cap on the fluid connector, further securing the tubular connector within the fluid connector, arranging a tester tool on the optical assurance cap, the tester tool comprising a light source and a light sensor spaced an axial distance apart from one another, emitting a light from the light source, the light transmitting into the optical assurance cap, transmitting the light through a first section having a first light absorption coefficient, transmitting the light through a second section having a second light absorption coefficient, and detecting the light emitted from the light source via the light sensor.

Even further, the present disclosure broadly includes an optical assurance cap, including a body including a through-bore, a first cavity filed with a first gas, the first gas having a first light absorption coefficient, a second cavity filed with a second gas, the second gas having a second light absorption coefficient, and a first section having a third light absorption coefficient, operatively arranged between the first cavity and the second cavity, wherein the first and second light absorption coefficients form a first combined light absorption coefficient, and the first, second, and third light absorption coefficients form a second combined light absorption coefficient, the first combined light absorption coefficient being less than the second combined light absorption coefficient.

A primary object of this disclosure is to provide an optical assurance cap which utilizes a photoelectric sensor in order to determine if the assurance cap is properly seated. The assurance cap itself is made of a material having a first light absorption coefficient with a ring made from another material having a second light absorption coefficient positioned in the middle of the body of the cap. The ring prevents light from passing though the body of the assurance cap. This blockage through the assurance cap forces the light to deflect out of the cap and into a through-bore arranged within the fluid connector, where the tubular connector and fluid connector are arranged. If the assurance cap is not fully seated on the fluid connector, light will deflect out of the assurance cap and be able to pass through a gap formed between the fluid connector and assurance cap. This deflected light can then be read by a sensor positioned around the assembly. If sufficient deflected light is detected by the sensor, a manufacturing system or user will be notified that the assurance cap and tubular connector are not properly secured to the fluid connector.

These and other objects, features and advantages of the present disclosure will become readily apparent upon a review of the following detailed description, in view of the drawings and appended claims.

BRIEF DESCRIPTION OF THE DRAWINGS

The nature and mode of operation of the present disclosure will now be more fully described in the following detailed description of the disclosure taken with the accompanying figures, in which.

DETAILED DESCRIPTION

Figure 1:
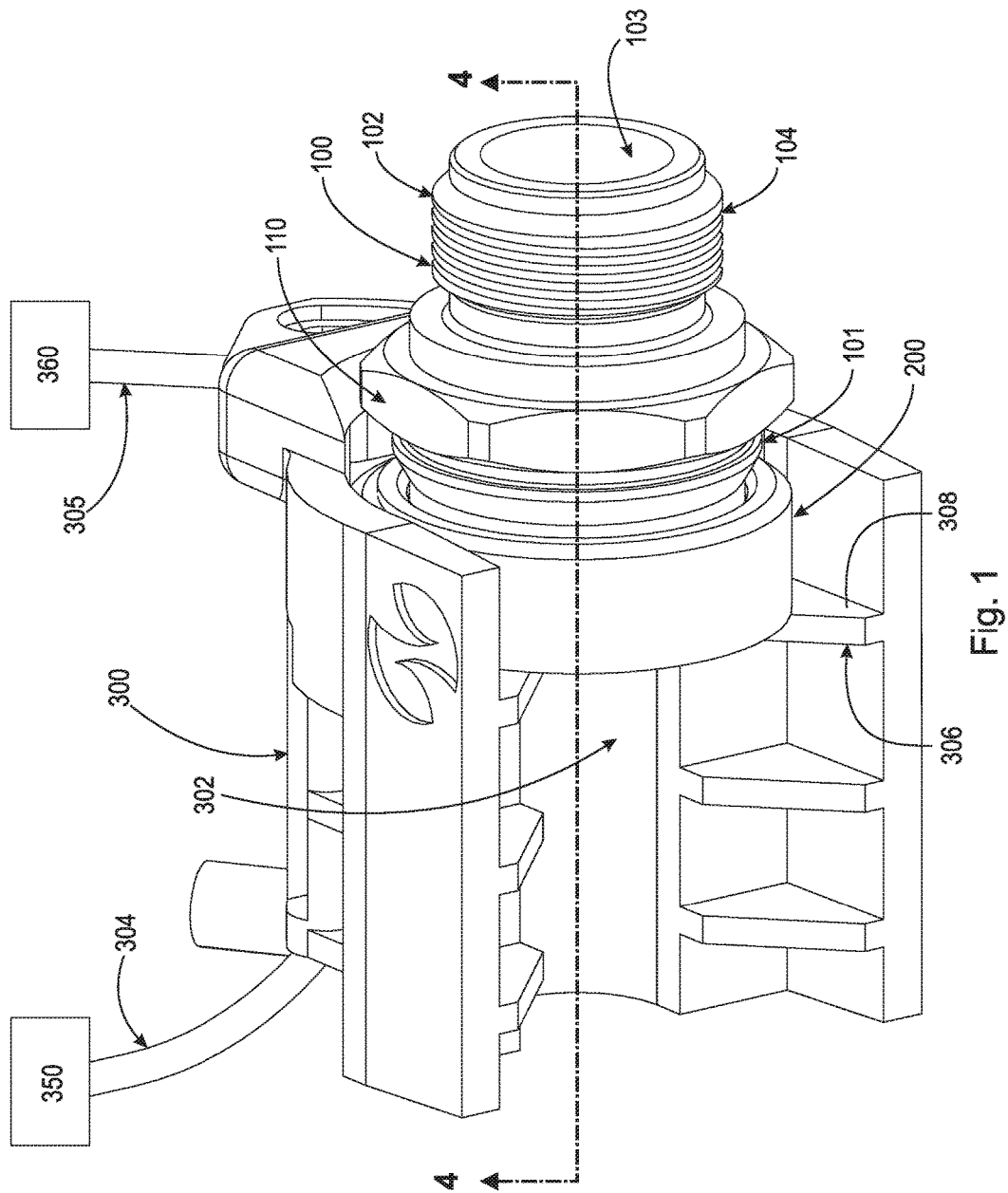
FIG. 1 is a perspective view of a fluid connector, an optical assurance cap, and a tester tool.

At the outset, it should be appreciated that like drawing numbers on different drawing views identify identical, or functionally similar, structural elements of the disclosure. It is to be understood that this disclosure is not limited to the disclosed aspects.

Furthermore, it is understood that this disclosure is not limited to the particular methodology, materials and modifications described and, as such, may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing. For the purposes of describing the present disclosure, the term "light absorption" should be understood to mean "the removal of energy or particles from a beam of light by the medium through which the beam propagates." The light absorption coefficient determines how far into a material light of a particular wavelength can penetrate before it is absorbed. In a material with a low light absorption coefficient, light is only poorly absorbed, and if the material is thin enough, it will appear transparent to that wavelength. The light absorption coefficient depends on the material and also on the wavelength of light which is being absorbed. The absorption coefficient ranges from 0 to 1: the higher the absorption coefficient, the more absorption that occurs within a material. When light passes through two materials having different light absorption coefficients, the absorption is additive. For example, if a first material absorbs 90% of light propagating through it, and a second section absorbs 10% of the same light propagating through it, the final light absorption would be 91% of total light propagating through the two materials. (If 100 light units are passed through the first material, only 10 light units will pass through to the second material. Of those remaining 10 light units, 1 will be absorbed by the second material, and 9 will pass through. Thus, the final light absorption is 91%.)

Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. Additionally, the terms transparent, translucent, and opaque can correspond to certain light absorption coefficients. "Transparent" should be understood as "allowing all light to pass through a material" and having a light absorption coefficient of 0. "Translucent" should be understood as "allowing some light to pass through a material" and having a light absorption coefficient range of approximately 0.01 to 0.99. "Opaque" should be understood as "preventing a substantial or complete amount of light from passing through a material" and having an absorption coefficient of 1.

Adverting now to the figures, FIG. 1 is a perspective view of fluid connector 100, optical assurance cap 200, and tester tool 300. Optical assurance cap 200 secures to fluid connector 100 on section 101. Section 102 of fluid connector 100 comprises threads 104 which allow fluid connector 100 to secure to an apparatus such as a transmission, radiator, oil cooler, etc. Fluid connector 100 also includes head 110 which allows a user to use a tool such as a wrench to screw fluid connector 100 into a corresponding apparatus (not shown). Through-bore 103 is arranged in the center of fluid connector 100 and passes through the whole body of fluid connector 100. Tester tool 300 includes channel 302 and rib 306. Optical assurance cap 200 is arranged within channel 300 and abuts against surface 308 of rib 306. In an example embodiment, optical lines 304 and 305 are operatively arranged within tester tool 300 and are connected to light source 350 and light sensor 360. In an example embodiment, light sensor 360 is a phototransistor or some other light detecting sensor which can detect transmitted light passing through optical lines 304 and 305. It should be appreciated, however, that optical lines 304 and 305 could be arranged within testing tool 300, having light source 350 and light sensor 360 also arranged within tester tool 300. Optical lines 304 and 305 channel fiber-optic light in order to test if light escapes from a gap formed between fluid connector 100 and optical assurance cap 200. If light escapes from the connection between fluid connector 100 and optical assurance cap 200, optical assurance cap 200 is not fully seated on fluid connector 100. It should be appreciated that either optical line 304 or optical line 305 could emit or receive light from the opposite, corresponding optical line. A suitable example of light source 350 and light sensor 360 include, but is not limited to, the FS-N or NEO Series Digital Fiber Optic Sensors sold by Keyence Corporation of America (Itasca, Ill.). Although the foregoing optic sensor includes both a light source and a light sensor in a single unit, it is within the scope of the claims to use a light source which is separate from a light sensor. Additionally, other forms of light and conductors could be used besides light emitted from an LED source 350 and channeled through optical fibers in order to detect light emission from the connection between fluid connector 100 and optical assurance cap 200.

Figure 2A:
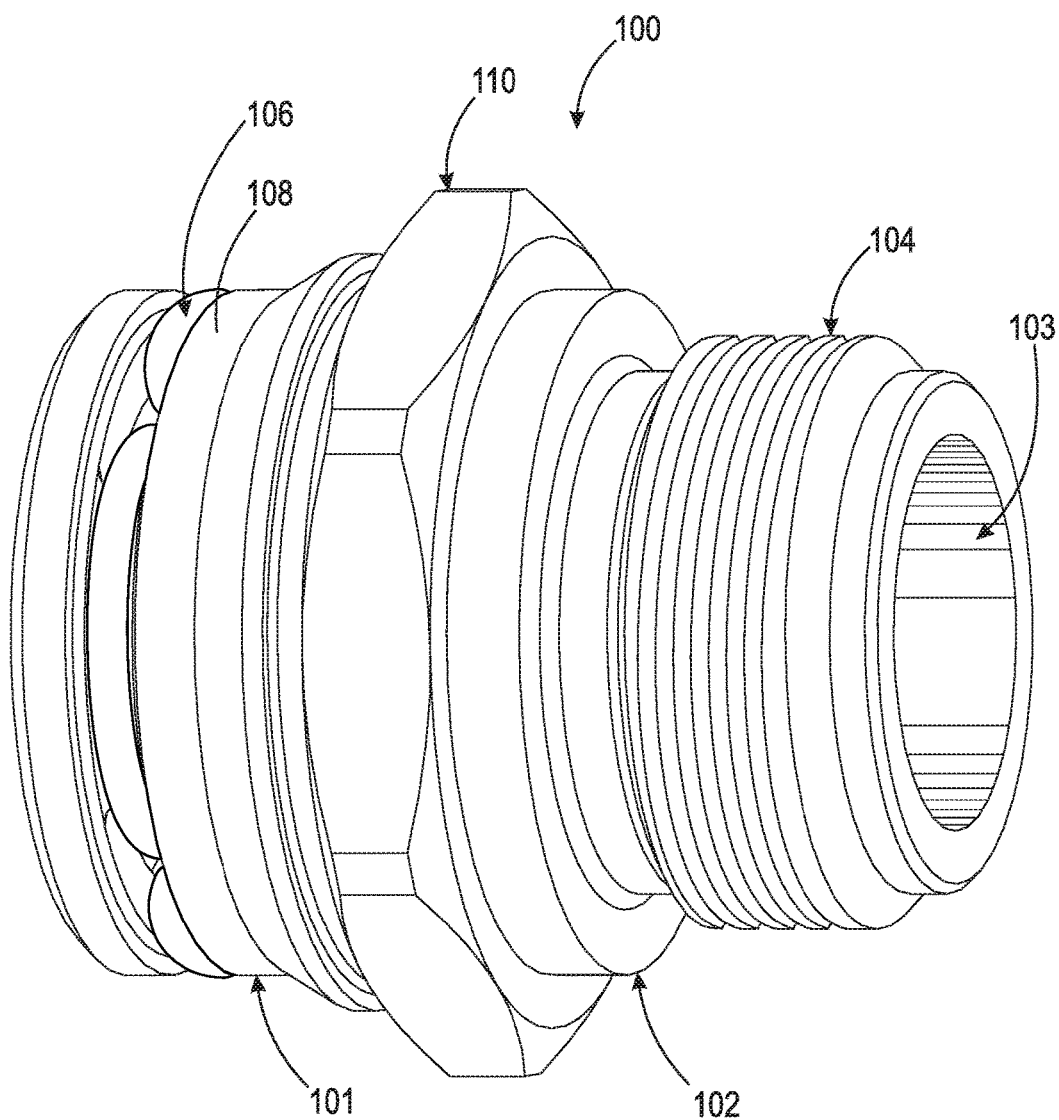
FIG. 2A is a front perspective view of the fluid connector.
Figure 2B:
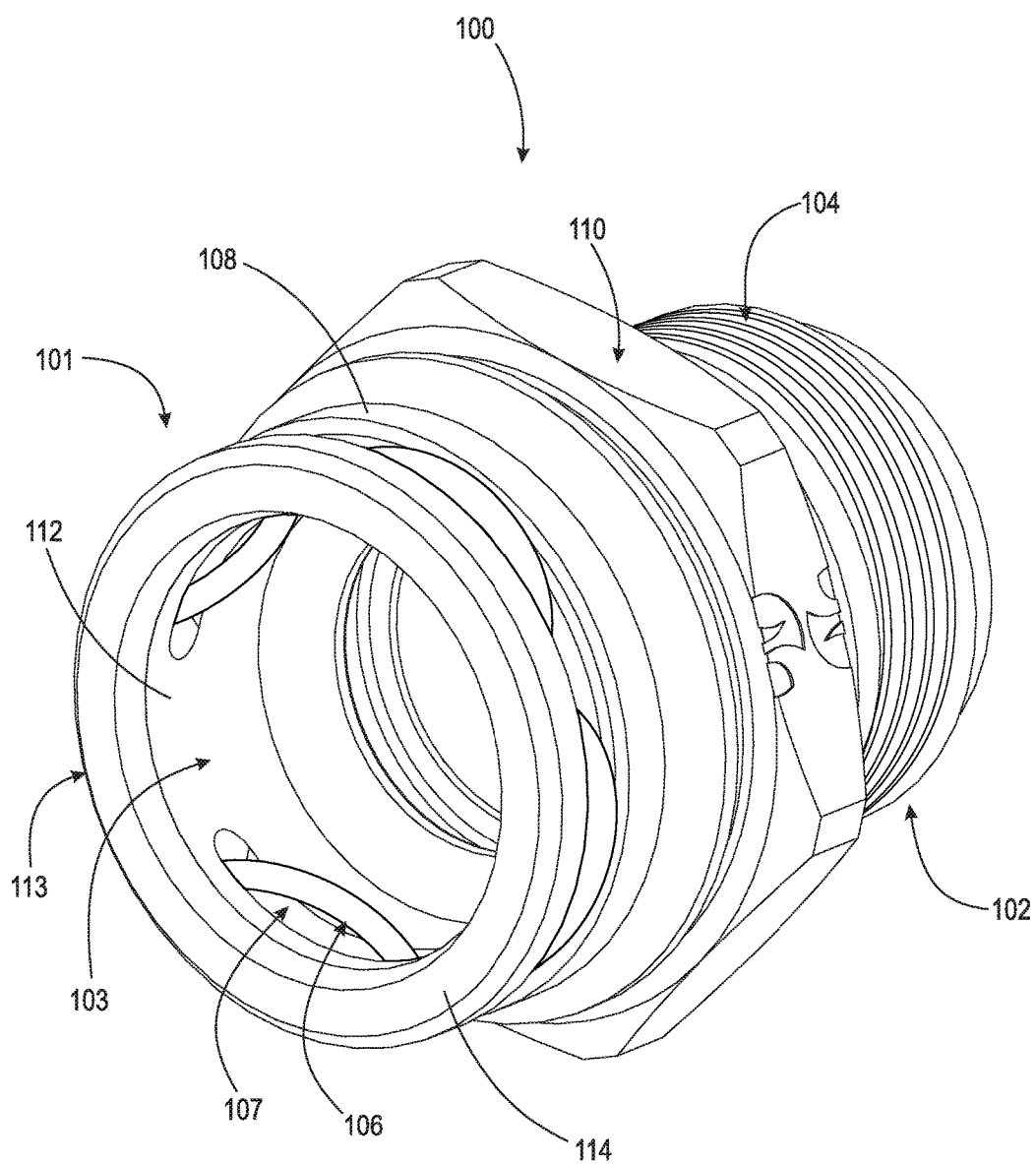
FIG. 2B is a rear perspective view of the fluid connector.

FIG. 2A and FIG. 2B are a front perspective view and a rear perspective view of fluid connector 100, receptively. Fluid connector 100 comprises section 101 and section 102. Section 101 includes snap ring 106, outer surface 108, inner surface 112, shoulder 113, and shoulder surface 114. Snap ring 106 engages optical assurance cap 200 and connects fluid connector 100 with optical assurance cap 200. Snap ring 106 is arranged within apertures 107 of fluid connector 100 and secures tubular connector 500 (shown in FIG. 4A) within through-bore 103 of fluid connector 100.

Figure 3A:
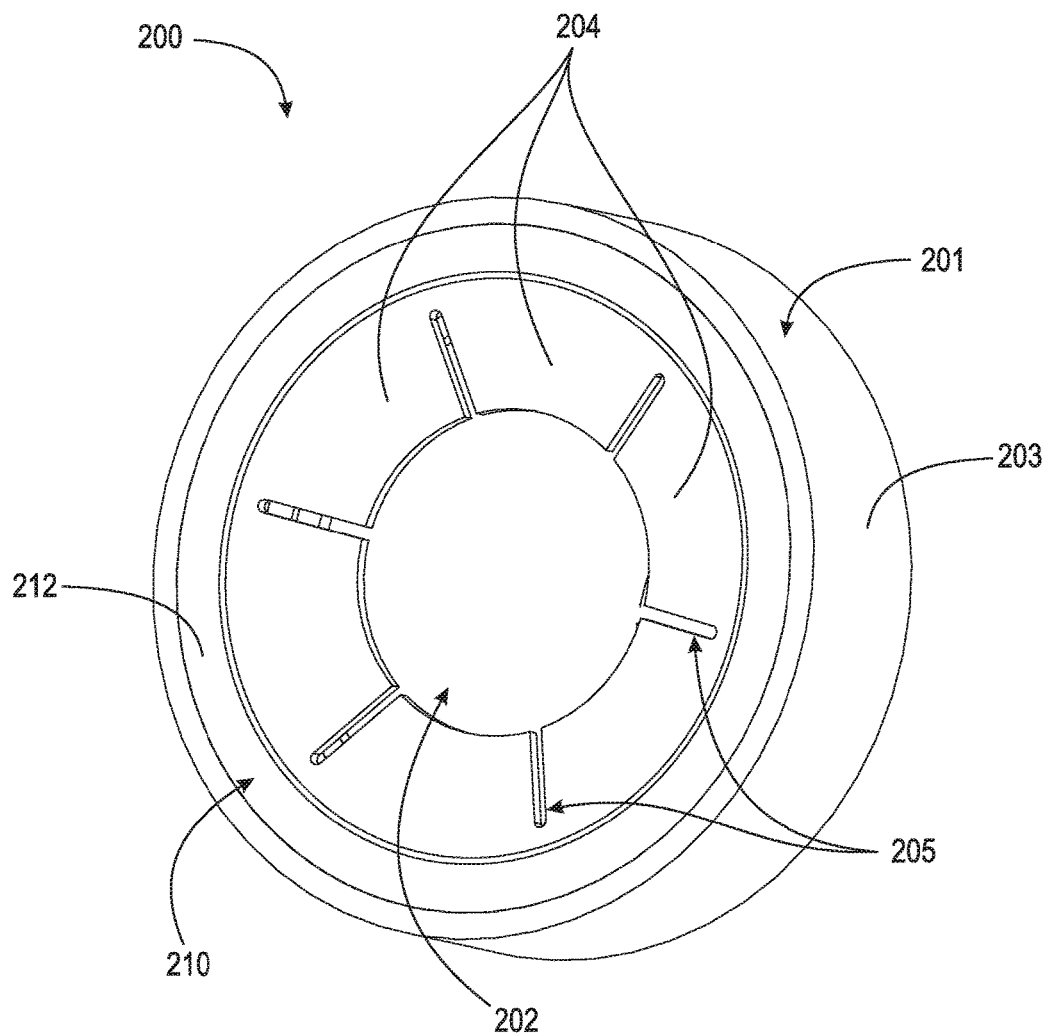
FIG. 3A is a front perspective view of the optical assurance cap.
Figure 3B:
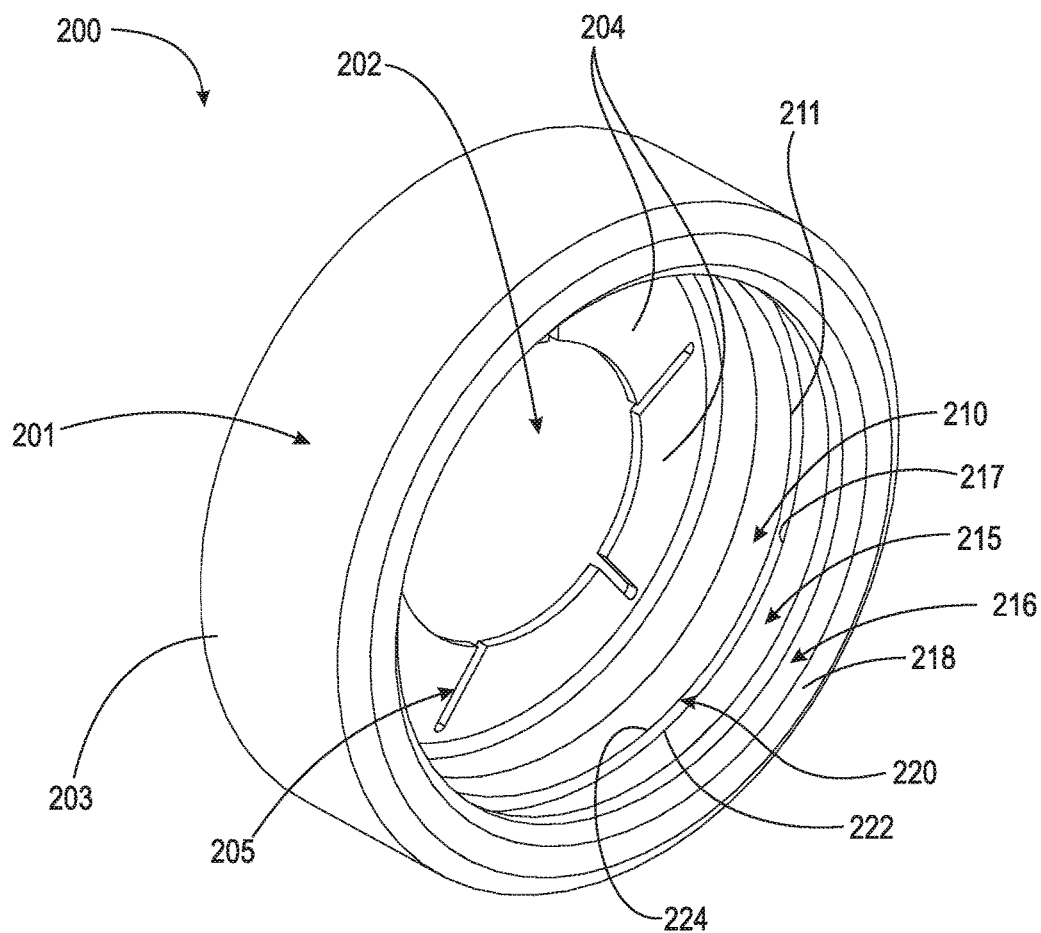
FIG. 3B is a rear perspective view of the optical assurance cap.

FIG. 3A and FIG. 3B are a front perspective view and a rear perspective view of optical assurance cap 200, respectively. Optical assurance cap 200 broadly comprises body 201, through-bore 202, outer surface 203, tabs 204, relief cuts 205, section 210, section 215, shoulder 216, and section 220. Through-bore 202 is arranged within body 201 and allows tubular connector 500 or hose 502 (shown in FIG. 4A) to pass through optical assurance cap 200 to secure to fluid connector 100. Tabs 204 are arranged on section 210 and extend radially inward towards through-bore 202. Additionally, tabs 204 engage hose 502 in order to center optical assurance cap 200 on fluid connector 100. Relief cuts 205 are operatively arranged on tabs 204 to allow tabs 204 to deform around a non-linear object, such as hose 502 (shown in FIG. 4A) arranged within the engine bay of an automobile. In an example embodiment, tabs 204 are translucent and integral with section 210 while body 201 is opaque, or has a light absorption coefficient greater than zero.

Sections 210 and 215 are arranged within through-bore 202 of body 201. Section 220 is integral with body 201 and arranged between sections 210 and 215. Surface 211 of section 210 abuts against surface 224 of section 220 and surface 217 of section 215 abuts against surface 222 of section 220. In an example embodiment, due to the placement of section 220, light cannot pass directly from section 210 to section 215 without first transmitting into through-bore 202. It should be appreciated, however, that light could pass through sections 210, 215 and 220, each section having a different light absorption coefficient. Shoulder 216 is integral with section 215 and is translucent itself. Shoulder 216 includes surface 218 and secures optical assurance cap 200 to fluid connector 100 via an interaction with snap ring 106 (shown in FIG. 3A). Sections 210, 215, and 220 can be transparent, translucent, or opaque, depending on which specific combination of light absorption is required.

Figure 4A:
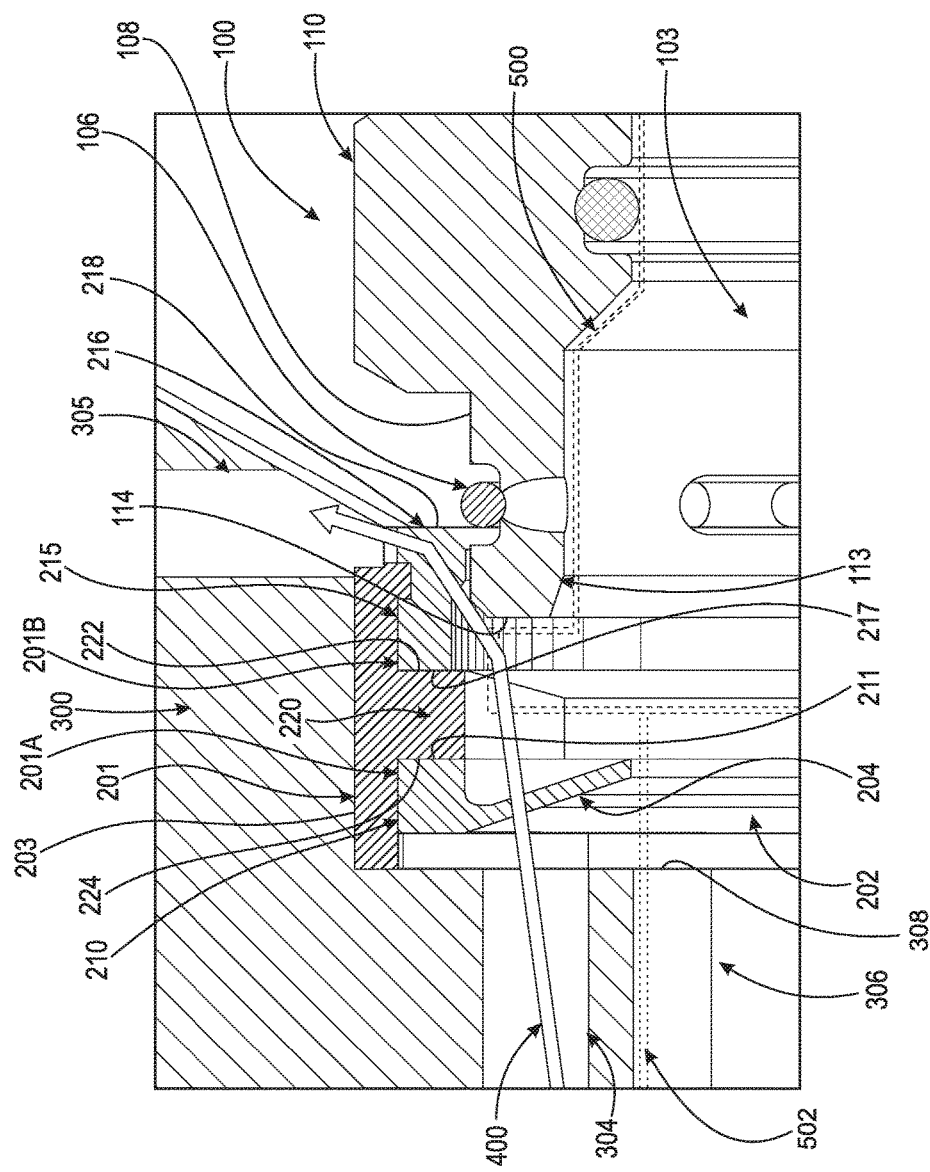
FIG. 4A is a detailed cross-sectional view of the fluid connector, optical assurance cap, and tester tool taken generally along line 4-4 in FIG. 1 with the optical assurance cap not fully seated on the fluid connector.
Figure 4B:
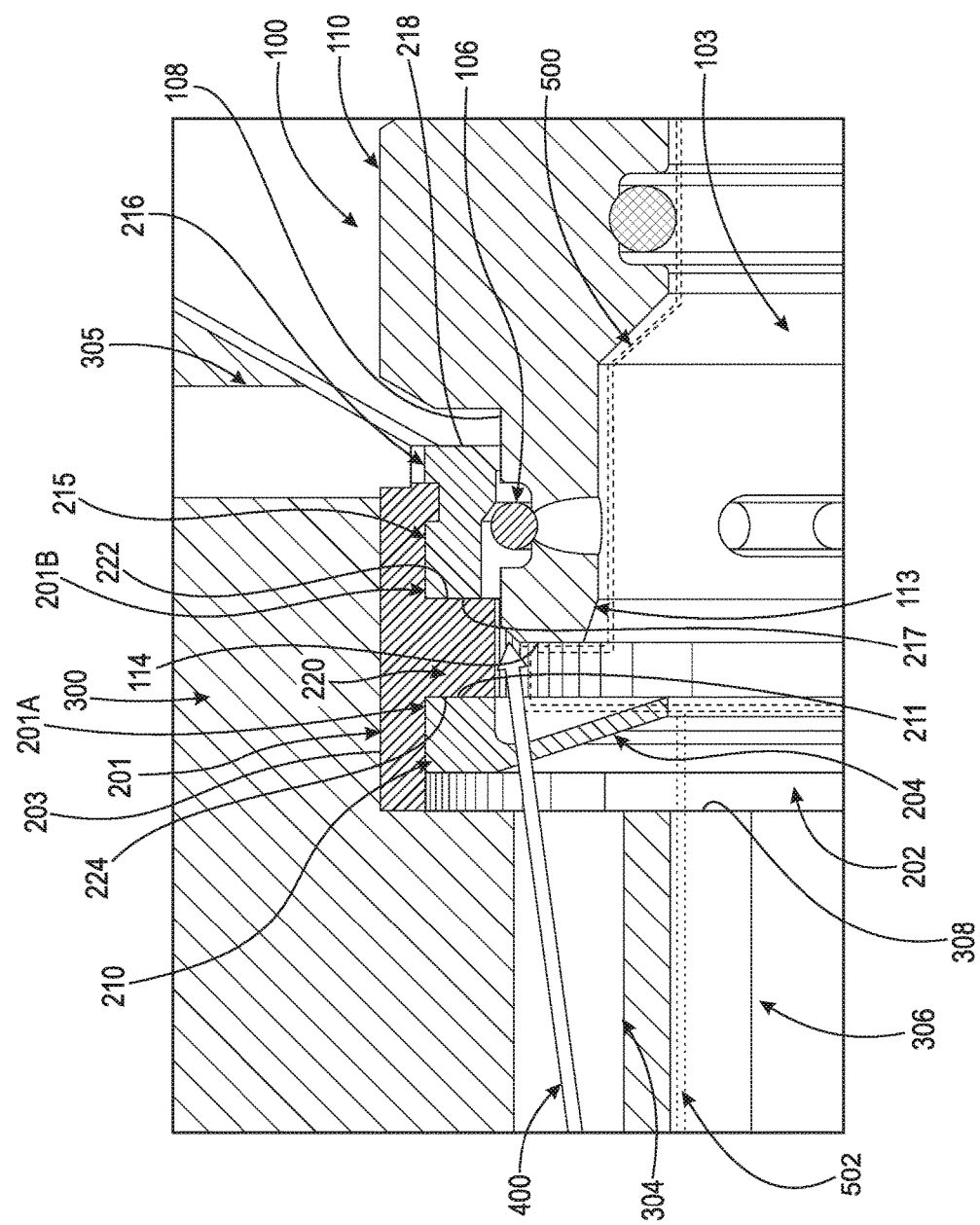
FIG. 4B is a detailed cross-sectional view of the fluid connector, optical assurance cap, and tester tool taken generally along line 4-4 in FIG. 1 with the optical assurance cap fully seated on the fluid connector.
Figure 5A:
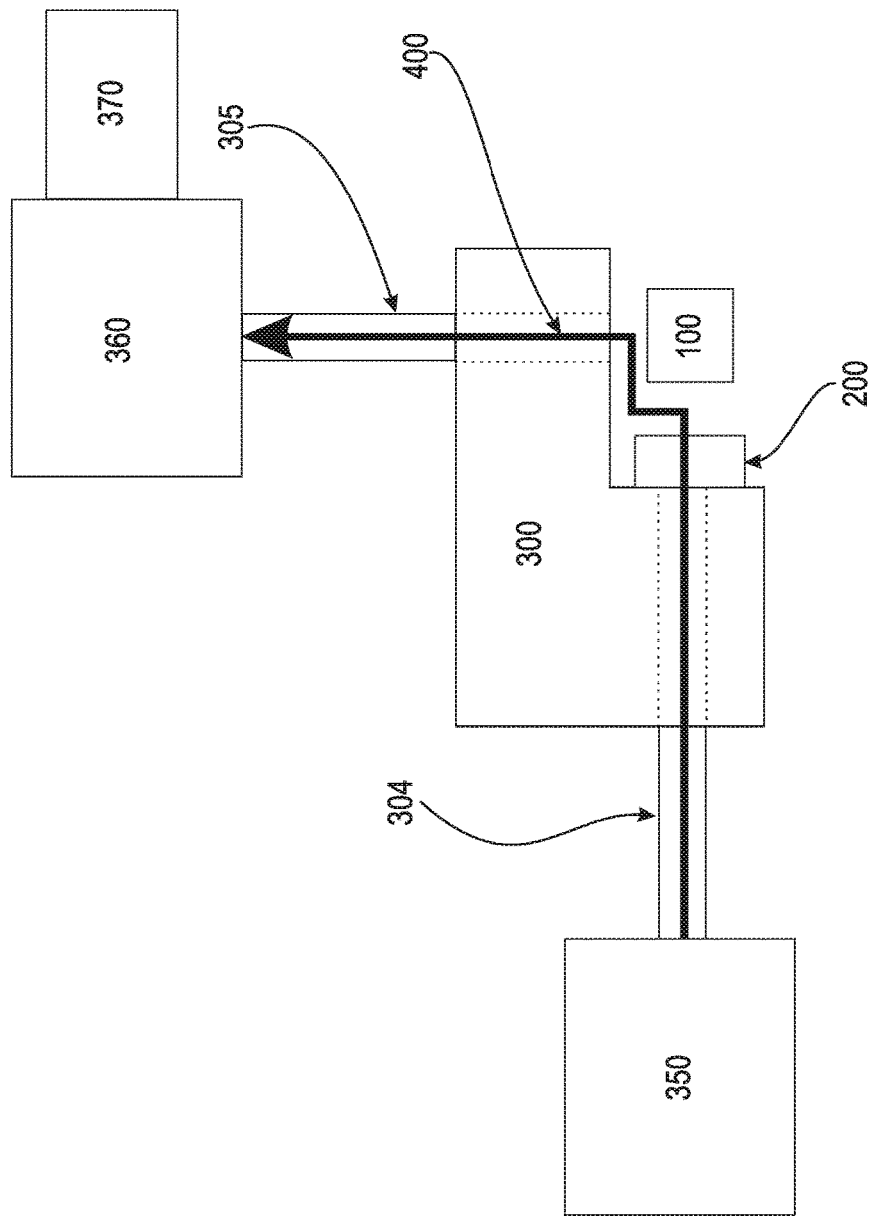
FIG. 5A is a schematic view of the fluid connector, optical assurance cap, and tester tool with the optical assurance cap not fully seated on the fluid connector.

FIG. 4A and FIG. 5A are a detailed cross-sectional view taken generally along line 4-4 in FIG. 1 and a schematic view of fluid connector 100, optical assurance cap 200, and tester tool 300 with optical assurance cap 200 not fully seated on fluid connector 100, respectively. Tubular connector 500 and hose 502 are represented in FIGS. 4A and 4B as dashed outlines for clarity. It should be understood that tubular connector 500 and hose 502 are solid bodies arranged within the assembly. Optical assurance cap 200 is concentrically arranged on hose 502 and interacts with hose 502 via tabs 204. Tubular connector 502 is inserted into through-bore 103 of fluid connector 100 and secured within fluid connector 100 by snap ring 106. Optical assurance cap 200 is slid down hose 502 and secured over tubular connector 502. As a secondary securement means, optical assurance cap 200 is operatively arranged to secure over tubular connector 500 and fluid connector 100. Additionally, optical assurance cap 200 acts as a secondary testing means to determine if tubular connector 500 is fully inserted into fluid connector 100.

Sections 210 and 215 are arranged within the inner circumference of body 201. Body 201 includes channels 201A and 201B, which are circumferentially arranged within body 201 and are spaced an axial distance apart. Section 220 is arranged in the axial gap between sections 210 and 215 and prevents light from directly passing from section 210 to section 215. In an example embodiment, sections 210 and 215 are annular rings made from a material which allows light to pass through them. For light to pass though optical assurance cap 200, light must pass through outer surface 212 of section 210, then transmit from section 210 into through-bore 202, and then transmit into section 215. In an example embodiment, section 210 and section 215 are made from a translucent material and section 220 is made from an opaque material. It should be appreciated, however, that the use of different materials, each having a different corresponding light absorption coefficient, can be used. The light absorption coefficient characteristic of a material is dependent on the wavelength of the light propagating through the material. The light absorption coefficient is also a function of the thickness of the material that the light is propagating through. In the present disclosure, section 210 has a first light absorption coefficient, section 215 has a second light absorption coefficient, and section 220 has a third light absorption coefficient. It should be appreciated that the first light absorption coefficient can be greater than the second light absorption coefficient; the first light absorption coefficient can be less than the second light absorption coefficient; or the first light absorption coefficient can be equal to the second light absorption coefficient. Additionally, the first light absorption coefficient and/or second light absorption coefficient can be less than the third light absorption coefficient. This arrangement of the first, second, and third light absorption coefficients form a first combined light absorption coefficient between the first light absorption coefficient and second light absorption coefficient, and a second combined light absorption coefficient between the first, second, and third light absorption coefficients, where the second combined light absorption coefficient is greater than the first combined light absorption coefficient. This difference between the first combined light absorption coefficient and the second combined light absorption coefficient is what is detected by light sensor 360. In an example embodiment, section 220 would have a light absorption coefficient that blocks a substantial amount of light, so much so that light sensor 360 could not detect any light if optical assurance cap 200 was fully seated.

To test if optical assurance cap 200 is fully seated on fluid connector 100, tester tool 300 is abutted against optical assurance cap 200 via surface 308 of rib 306. Tester tool 300 is designed in such a way as to block a substantial amount of surrounding light in order to achieve an accurate reading. Once tester tool 300 is operatively arranged on optical assurance cap 200, light 400 is emitted from light source 350 through optical line 304. Simultaneously, light sensor 360 detects the amount of light 400 which is transmitted through optical line 305. If optical assurance cap 200 is not fully seated on fluid connector 100, light 400 is able to pass through the gap formed between optical assurance cap 200 and fluid connector 100. As light 400 passes through the gap, transmitted light 400 is detected by light sensor 360 attached to optical line 305, which then outputs the detection of light 400 to output 370, which displays a corresponding value to the amount of light 400 detected by light sensor 360. It should be appreciated that output 370 is not limited to visual indicators, but can include other notification means, such as audible indicators or digital output to manufacturing systems. A user using tester tool 300 could check the valve represented on screen 370 to ensure no light is being detected by light sensor 360. If screen 370 displays a value greater than a threshold valve, the user then knows that light sensor 360 is receiving light 400 and that optical assurance cap 200 is not fully seated on fluid connector 100. If optical assurance cap 200 is not fully seated, there is also the possibility that tubular connector 500 is not fully seated within fluid connector 100. The detection of light 400 by light sensor 360 and corresponding output to screen 370 could inform a user of improper assembly of fluid connector 100, optical assurance cap 200, and tubular connector 500. This allows a user to reassemble the assembly so that a leak path does not form once the system is pressurized. Light 400 can be any frequency suitable for transmitting and detecting light emission from the assembly. Additionally, it should be appreciated that a plurality of optical lines 304 connected to light source 350 and a plurality of optical lines 305 connected to light sensor 360 could be used in order to test the connection between fluid connector 100 and optical assurance cap 200. Using a plurality of optical lines 304 and 305 would ensure that optical assurance cap 200 is fully seated on fluid connector 100, and not partially seated only on a single side.

Figure 5B:
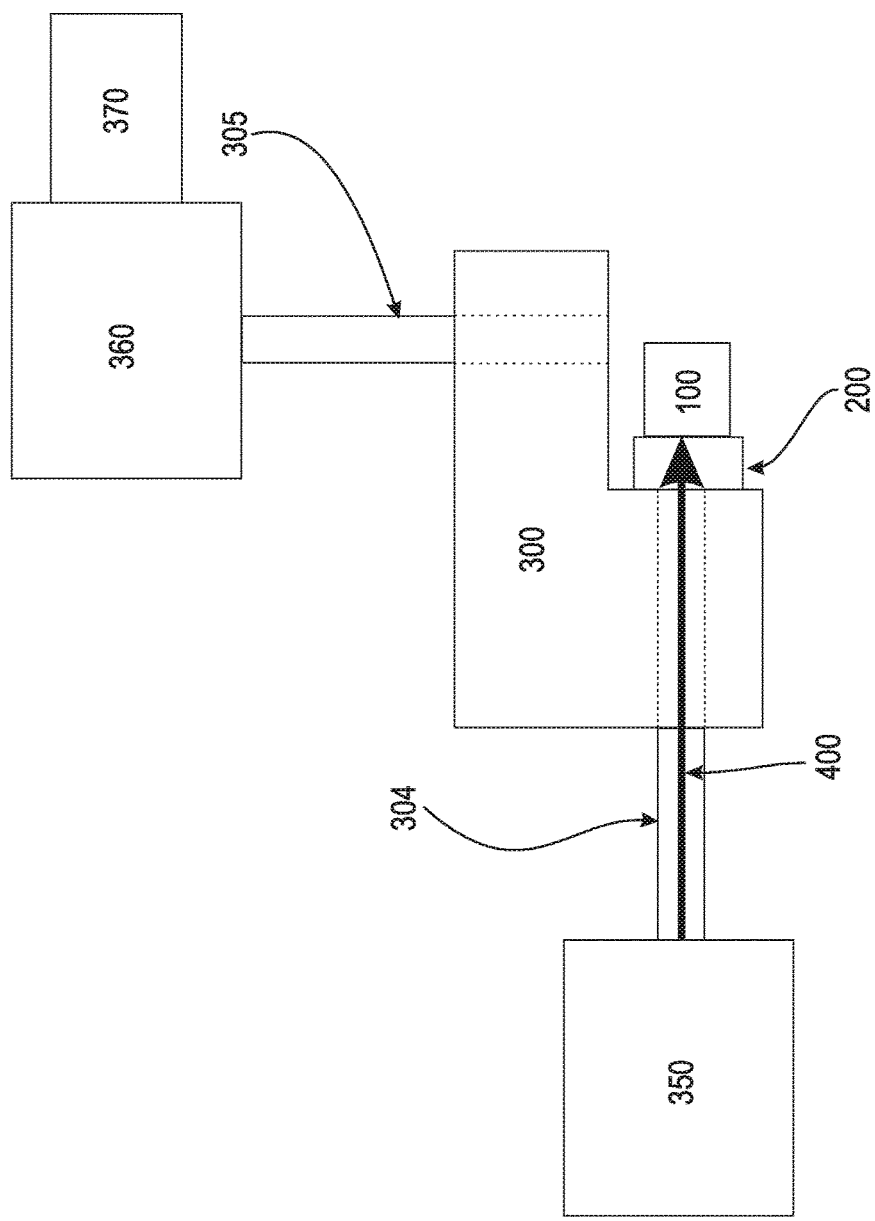
FIG. 5B is a schematic view of the fluid connector, optical assurance cap, and tester tool with the optical assurance cap fully seated on the fluid connector; and, FIG. 6A is a detailed cross-sectional view of the fluid connector, a second example embodiment of optical assurance cap, and tester tool taken generally along line 4-4 in FIG. 1 with the optical assurance cap not fully seated on the fluid connector; and, FIG. 6B is a detailed cross-sectional view of the fluid connector, the second example embodiment of optical assurance cap, and tester tool taken generally along line 4-4 in FIG. 1 with the optical assurance cap fully seated on the fluid connector.

FIG. 4B and FIG. 5B are a detailed cross-sectional view taken generally along line 4-4 in FIG. 1 and a schematic view of fluid connector 100, optical assurance cap 200, and tester tool 300 with optical assurance cap 200 fully seated on fluid connector 100, respectively. Optical assurance cap 200 secures to fluid connector 100 via shoulder 216 securing over snap ring 106. Shoulder 216 is integral with section 215 and manufactured from the same translucent material as section 210 and 215. If optical assurance cap 200 is fully seated on fluid connector 100, then light 400 emitted from optical line 304 passes through tabs 204 and section 210, transmits into through-bore 202, but is prevented from transmitting into section 215. If light 400 is blocked from transmitting into section 215, then light sensor 360 will receive an amount of light 400 below a threshold valve and output a corresponding value to screen 370. The value represented on screen 370 will inform a user that optical assurance cap 200 is fully seated on fluid connector 100. It should be appreciated; however, that light source 350 and light sensor 360 can be secured to either optical line 304 or 305. Light 400 can be prevented from traveling between sections 210 and 215, with disregard to the direction of light transmission.

The method of detecting the axial position of optical assurance cap 200 with respect to fluid connector 100 begins with assembling the components. First, tubular connector 500 is inserted into through-bore 103 of fluid connector 100. Optical assurance cap 200 is then secured over fluid connector 100 and tubular connector 500 operatively arranged within through-bore 103. Tester tool 300 is then arranged over optical assurance cap 200 [most sensors only detect the specific wavelength]. Light source 350, arranged within tester tool 300, then emits light 400. Light 400 is transmitted through optical line 304 and into section 210 of optical assurance cap 200. Light 400 then transmits out of section 210 and into through-bore 103. Simultaneously, light sensor 360 is detecting any light which is transmitted through optical line 305. If optical assurance cap 200 is not fully seated on fluid connector 100, then light 400 can transmit to section 215. Light 400 then transmits to optical line 305 and is able to be detected light sensor 360. As light 400 reaches light sensor 360, light sensor 360 detects the amount of light 400 present and then outputs a corresponding value to screen 370. A user then can ensure that the value represented on screen 370 is within an acceptable range of light detection, or to ensure there is an absence of light 400 reaching light sensor 360.

Figure 6A:
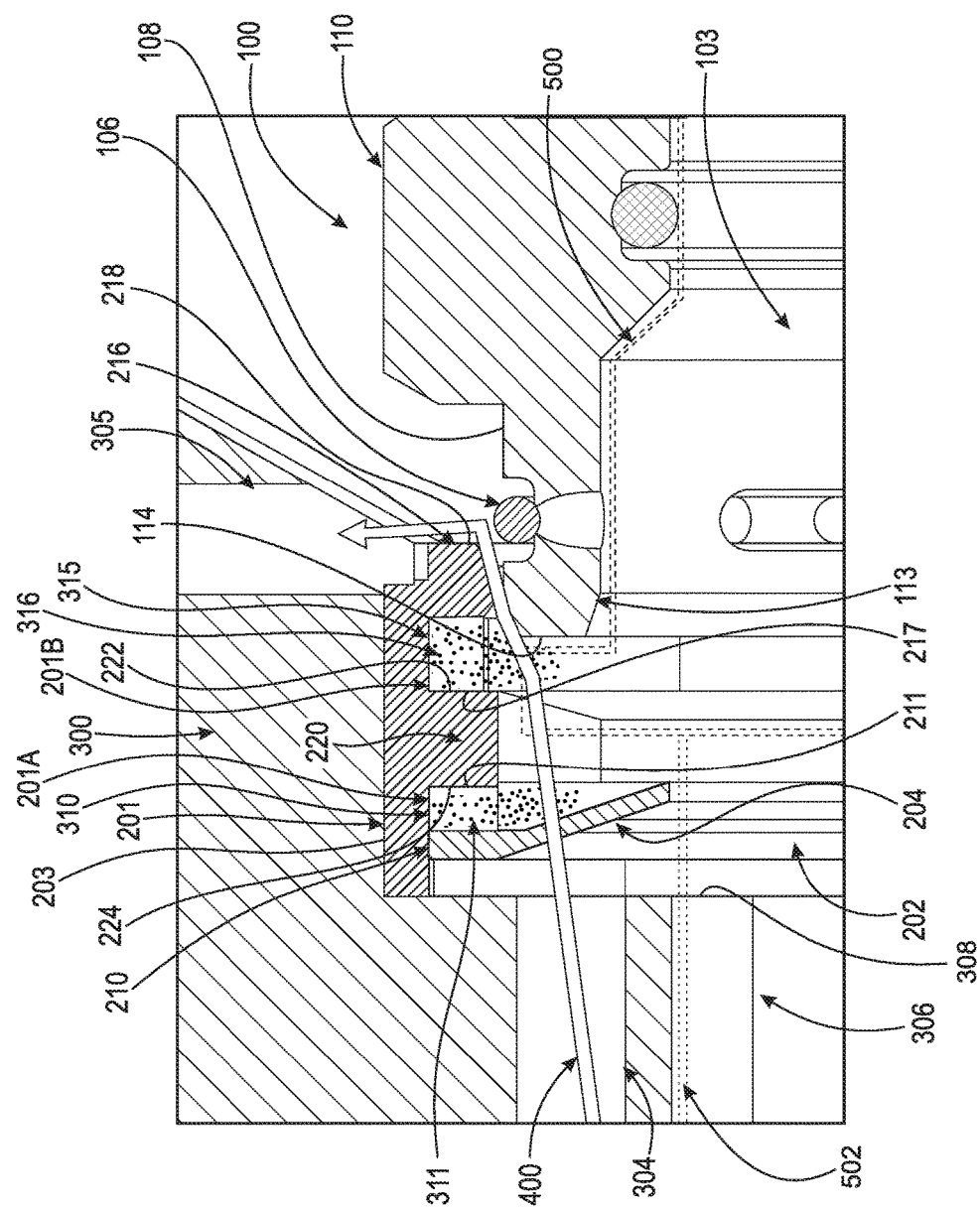
Figure 6B:
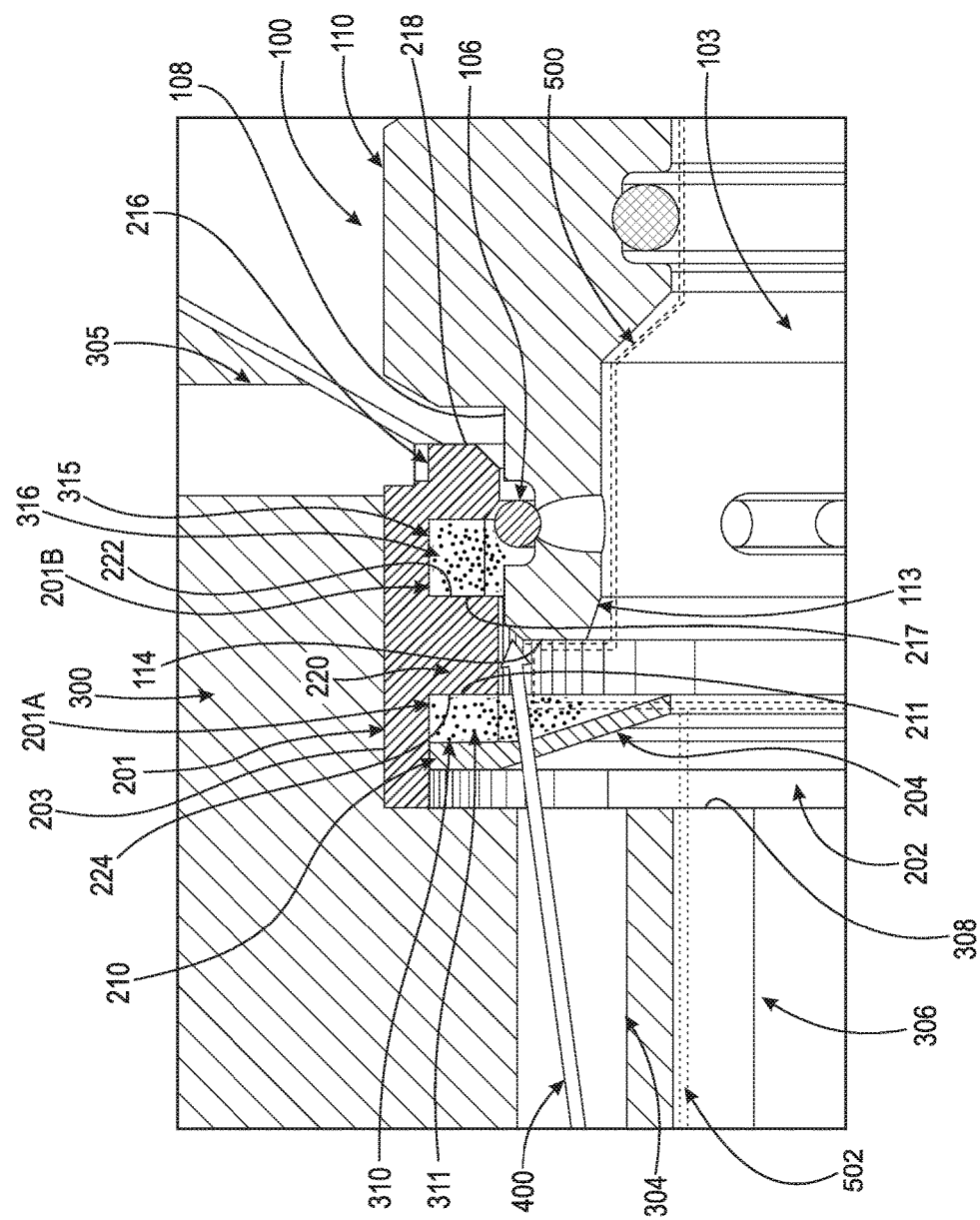

FIG. 6A and FIG. 6B are a detailed cross-sectional view taken generally along line 4-4 in FIG. 1 of fluid connector 100, a second example embodiment of optical assurance cap 200, and tester tool 300. In the second embodiment of optical assurance cap 200, channels 201A and 201B form cavities 310 and 315, respectively. Cavities 310 and 315 are field with gas 311 and gas 316, respectively. In a preferred embodiment, gas 311 and gas 316 are stable gases such as ambient air. However, it should be appreciated, that other gases could be used such as nitrogen, argon, helium, and/or any other stable gas. As light 400 passes through gas 311 and gas 316, light is absorbed similarly to light absorption within section 210 and section 215. The light absorption coefficient characteristic of a material is dependent on the wavelength of the light propagating through the material. The light absorption coefficient is also a function of the thickness of the material that the light is propagating through. In the present disclosure, gas 311 has a first light absorption coefficient, gas 316 has a second light absorption coefficient, and section 220 has a third light absorption coefficient. It should be appreciated that the first light absorption coefficient can be greater than the second light absorption coefficient; the first light absorption coefficient can be less than the second light absorption coefficient; or the first light absorption coefficient can be equal to the second light absorption coefficient. Additionally, the first light absorption coefficient and/or second light absorption coefficient can be less than the third light absorption coefficient. This arrangement of the first, second, and third light absorption coefficients form a first combined light absorption coefficient between the first light absorption coefficient and second light absorption coefficient, and a second combined light absorption coefficient between the first, second, and third light absorption coefficients, where the second combined light absorption coefficient is greater than the first combined light absorption coefficient. This difference between the first combined light absorption coefficient and the second combined light absorption coefficient is what is detected by light sensor 360. In an example embodiment, section 220 would have a light absorption coefficient that blocks a substantial amount of light, so much so that light sensor 360 could not detect any light if second example embodiment of optical assurance cap 200 was fully seated.

In the foregoing description, example embodiments are described. The specification and drawings are accordingly to be regarded in an illustrative rather than a restrictive sense.

It will be appreciated that various aspects of the above-disclosed disclosure and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

LIST OF REFERENCE NUMERALS

100 fluid connector
101 section
102 section
103 through-bore
104 threads
106 snap ring
107 apertures
108 surface
110 head
112 inner surface
113 shoulder
114 shoulder surface
200 optical assurance cap
201 body
202 through-bore
203 outer surface
204 tabs
205 relief cuts
210 section
211 surface
212 outer surface
215 section
216 shoulder
217 surface
218 surface
220 section
222 surface
224 surface
300 tester tool
302 channel
304 optical line
305 optical line
306 rib
308 surface
310 cavity
311 gas
315 cavity
316 gas
350 light source
360 light sensor
370 screen
400 light
500 tubular connector
502 hose

What is claimed is:

1. An optical assurance cap, comprising:
a body comprising:
a through-bore;
a first section having a first light absorption coefficient;
a second section having a second light absorption coefficient; and,
a third section having a third light absorption coefficient, operatively arranged between said first section and said second section,
wherein said first and second light absorption coefficients form a first combined light absorption coefficient, and said first, second, and third light absorption coefficients form a second combined light absorption coefficient, said first combined light absorption coefficient being less than said second combined light absorption coefficient.

2. The optical assurance cap as recited in claim 1, wherein said first light absorption coefficient is greater than said second light absorption coefficient, said first light absorption coefficient is less than said second light absorption coefficient, or said first light absorption coefficient is equal to said second light absorption coefficient.

3. The optical assurance cap as recited in claim 1, wherein, said first light absorption coefficient and/or said second light absorption coefficient is less than said third light absorption coefficient.

4. The optical assurance cap as recited in claim 1, wherein said first and second sections are annular rings.

5. The optical assurance cap as recited in claim 1, wherein said third section is integral with said body.

6. The optical assurance cap as recited in claim 1, further comprising a shoulder arranged on said second section and engages a fluid connector via said shoulder.

7. The optical assurance cap as recited in claim 1, wherein said body has a light absorption coefficient greater than zero.

8. The optical assurance cap as recited in claim 1, wherein said first section and said second section are translucent and said third section is opaque.

9. The optical assurance cap as recited in claim 1, wherein said first section and said second section are transparent and said third section is opaque.

10. The optical assurance cap as recited in claim 1, wherein said first section and said second section are translucent and said third section is translucent.

11. The optical assurance cap as recited in claim 1, wherein said first section and said second section are transparent and said third section is translucent.

12. An optical assurance cap, comprising:
a body comprising:
a through-bore;
a first inner circumferentially arranged channel; and,
a second inner circumferentially arranged channel;
a first section having a first light absorption coefficient, arranged within said first inner circumferentially arranged channel; and, a second section having a second light absorption coefficient, arranged within said second inner circumferentially arranged channel.

13. The optical assurance cap as recited in claim 12, wherein said first light absorption coefficient is greater than said second light absorption coefficient, said first light absorption coefficient is less than said second light absorption coefficient, or said first light absorption coefficient is equal to said second light absorption coefficient.

14. The optical assurance cap as recited in claim 12, wherein said first and second sections are annular rings.

15. The optical assurance cap as recited in claim 12, wherein said first and said second inner circumferentially arranged channels are axially displaced from one another.

16. The optical assurance cap as recited in claim 12, further comprising a third section having a third light absorption coefficient is arranged between said first and said second inner circumferentially arranged channels, said third section integral with said body.

17. The optical assurance cap as recited in claim 16, wherein said first and second light absorption coefficients form a first combined light absorption coefficient, and said first, second, and third light absorption coefficients form a second combined light absorption coefficient, said first combined light absorption coefficient being less than said second combined light absorption coefficient.

18. The optical assurance cap as recited in claim 16, wherein, said first light absorption coefficient and/or said second light absorption coefficient is less than said third light absorption coefficient.

19. A fluid connector assembly, comprising:
a fluid connector comprising a through-bore;
an optical assurance cap arranged on said fluid connector, said optical assurance cap comprising:
a first section having a first light absorption coefficient;
a second section having a second light absorption coefficient, comprising a shoulder to engage said fluid connector;
a third section having a third light absorption coefficient, arranged between said first section and said second section;
wherein said first and second light absorption coefficients form a first combined light absorption coefficient, and said first, second, and third light absorption coefficients form a second combined light absorption coefficient, said first combined light absorption coefficient being less than said second combined light absorption coefficient; and,
a through-bore operatively arranged in said first section, said second section, and said third section, aligning with said through-bore of said fluid connector; and,
a tubular connector arranged in said through-bore of said fluid connector and secured to said fluid connector by said optical assurance cap.

20. The optical assurance cap as recited in claim 19, wherein said first light absorption coefficient is greater than said second light absorption coefficient, said first light absorption coefficient is less than said second light absorption coefficient, or said first light absorption coefficient is equal to said second light absorption coefficient.

21. The optical assurance cap as recited in claim 19, wherein, said first light absorption coefficient and/or said second light absorption coefficient is less than said third light absorption coefficient.

22. A fluid connector assembly, comprising:
a fluid connector comprising a through-bore;
an optical assurance cap arranged on said fluid connector, said optical assurance cap comprising:
a through-bore;
a first section having a first light absorption coefficient;
a second section having a second light absorption coefficient; and,
a third section having a third light absorption coefficient;
a tubular connector arranged in said through-bore of said fluid connector and secured to said fluid connector; and,
a tester tool comprising:
a channel;
a light source; and,
a light sensor, said light source and said light sensor axially displaced from one another,
wherein said optical assurance cap is arranged in said channel of said tester tool.

23. The fluid connector assembly as recited in claim 22, wherein said optical assurance cap is arranged between said light source and said light sensor.

24. The fluid connector assembly as recited in claim 22, wherein:
said third section is operatively arranged between said first section and said second section; and,
said first and second light absorption coefficients form a first combined light absorption coefficient, and said first, second, and third light absorption coefficients form a second combined light absorption coefficient, said first combined light absorption coefficient being less than said second combined light absorption coefficient.

25. The fluid connector assembly as recited in claim 24, wherein said first light absorption coefficient is greater than said second light absorption coefficient, said first light absorption coefficient is less than said second light absorption coefficient, or said first light absorption coefficient is equal to said second light absorption coefficient.

26. The fluid connector assembly as recited in claim 24, wherein, said first light absorption coefficient and/or said second light absorption coefficient is less than said third light absorption coefficient.

27. The fluid connector assembly as recited in claim 22, wherein said light source emits fiber-optic light.

28. The fluid connector assembly as recited in claim 22, wherein said light sensor is a phototransistor.

29. A method of determining an optical assurance cap is fully seated on a fluid connector, the method comprising:
installing a tubular connector into a through-bore of said fluid connector;
installing said optical assurance cap on said fluid connector, further securing said tubular connector within said fluid connector;
arranging a tester tool on said optical assurance cap, said tester tool comprising a light source and a light sensor spaced an axial distance apart;
emitting a light from said light source, said light transmitting into said optical assurance cap;
transmitting said light through a first section having a first light absorption coefficient;
transmitting said light through a second section having a second light absorption coefficient; and,
detecting said light emitted from said light source via said light sensor.

30. The method as recited in claim 29, wherein said first light absorption coefficient is greater than said second light absorption coefficient, said first light absorption coefficient is less than said second light absorption coefficient, or said first light absorption coefficient is equal to said second light absorption coefficient.

31. The method as recited in claim 29, further comprising a third section having a third light absorption coefficient, arranged between said first section and said second section.

32. The method as recited in claim 31, wherein said first light absorption coefficient and/or said second light absorption coefficient is less than said third light absorption coefficient.

33. The method as recited in claim 31, wherein said first and second light absorption coefficients form a first combined light absorption coefficient, and said first, second, and third light absorption coefficients form a second combined light absorption coefficient, said first combined light absorption coefficient being less than said second combined light absorption coefficient.

34. An optical assurance cap, comprising:
  a body comprising:
    a through-bore;
    a first cavity filed with a first gas, said first gas having a first light absorption coefficient;
    a second cavity filed with a second gas, said second gas having a second light absorption coefficient; and,
    a first section having a third light absorption coefficient, operatively arranged between said first cavity and said second cavity,
  wherein said first and second light absorption coefficients form a first combined light absorption coefficient, and said first, second, and third light absorption coefficients form a second combined light absorption coefficient, said first combined light absorption coefficient being less than said second combined light absorption coefficient.

35. The optical assurance cap as recited in claim 34, wherein said first light absorption coefficient is greater than said second light absorption coefficient, said first light absorption coefficient is less than said second light absorption coefficient, or said first light absorption coefficient is equal to said second light absorption coefficient.

36. The optical assurance cap as recited in claim 34, wherein said first gas and said second gas are ambient air, nitrogen, argon, helium, and/or any stable gas.

\* \* \* \* \*